United States Patent [19]

Jahnke

[11] Patent Number: 4,659,492

[45] Date of Patent: Apr. 21, 1987

[54] ALKENYL-SUBSTITUTED CARBOXYLIC ACYLATING AGENT/HYDROXY TERMINATED POLYOXYALKYLENE REACTION PRODUCTS AND AQUEOUS SYSTEMS CONTAINING SAME

[75] Inventor: Richard W. Jahnke, Mentor, Ohio

[73] Assignee: The Lubrizol Corporation, Wickliffe, Ohio

[21] Appl. No.: 618,966

[22] Filed: Jun. 11, 1984

[51] Int. Cl.$^4$ ............... C10M 173/00; C10M 129/00
[52] U.S. Cl. ............... 252/49.3; 252/51.5 A; 252/56 D
[58] Field of Search ............... 252/49.3, 56 D, 51.5 A

[56] References Cited

U.S. PATENT DOCUMENTS

| | | | |
|---|---|---|---|
| Re. 30,885 | 3/1982 | Rieder | 252/34 |
| Re. 31,522 | 2/1984 | Rieder | 252/34 |
| 3,057,890 | 10/1962 | DeGroote | 252/56 D |
| 3,126,941 | 11/1965 | de Vries | 252/51.5 |
| 4,025,452 | 5/1977 | Nnadi et al. | 252/51.5 A |
| 4,239,635 | 12/1980 | Rieder | 252/49.3 |
| 4,253,975 | 3/1981 | Law et al. | 252/32.7 E |
| 4,379,063 | 4/1983 | Williams | 252/33.6 |
| 4,383,937 | 5/1983 | Williams | 252/389 R |
| 4,409,000 | 10/1983 | Williams | 44/70 |
| 4,448,703 | 5/1984 | Forsberg | 252/49.3 |

FOREIGN PATENT DOCUMENTS 0004426  3/1979  European Pat. Off.
0024848  8/1980  European Pat. Off.

OTHER PUBLICATIONS

Texaco Chemical Company, New Product Development, "Use of JEFFAMINE Products in Fuel and Lubricant Applications", (1985).

*Primary Examiner*—William R. Dixon, Jr.
*Assistant Examiner*—Cynthia A. Prezlock
*Attorney, Agent, or Firm*—Forrest L. Collins; James L. Cordek; Denis A. Polyn

[57] ABSTRACT

A composition is disclosed which comprises the water-dispersible reaction product of (A) at least one compound represented by the formula

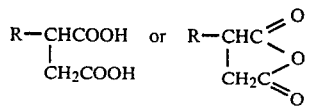

wherein R is an alkenyl group represented by the formula

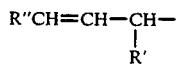

and R' and R" are independently hydrogen or straight chain or substantially straight chain hydrocarbyl groups of at least one carbon atom, with the proviso that R has from about 8 to about 30 carbon atoms, with (B) at least one water-soluble hydroxy terminated polyoxyalkylene. Aqueous concentrates and water-based functional fluids comprising these compositions are also disclosed.

20 Claims, No Drawings

ALKENYL-SUBSTITUTED CARBOXYLIC ACYLATING AGENT/HYDROXY TERMINATED POLYOXYALKYLENE REACTION PRODUCTS AND AQUEOUS SYSTEMS CONTAINING SAME

TECHNICAL FIELD

This invention relates to water-dispersible reaction products of at least one alkenyl-substituted carboxylic acrylating agent with at least one hydroxy terminated polyoxyalkylene and to aqueous systems containing such reaction products. The aqueous systems encompass both concentrates and water-based functional fluids, such as water-based lubricants, hydraulic fluids, cutting fluids and the like. The water-dispersible alkenyl-substituted carboxylic acylating agent/hydroxy terminated polyoxyalkylene reaction products are useful as thickeners for such aqueous systems; these reaction products are stable under relatively high shear conditions.

BACKGROUND OF THE INVENTION

The term "water-based functional fluid" is used herein to refer to water-based lubricants, hydraulic fluids, cutting fluids and the like. Water-based functional fluids are not a new concept. However, in recent times, the increasing cost and scarcity of petroleum has made it increasingly desirable to replace oil-based functional fluids with water-based functional fluids wherever possible. Other benefits can also flow from such replacements such as decreased fire hazard and environmental pollution problems. In many cases, however, it is not feasible to make such replacements because the water-based functional fluids cannot be modified in their properties so as to perform to the same high degree as their oil-based counterparts. For example, it has been often difficult, if not impossible, to replace certain oil-based hydraulic fluids with water-based fluids even though the desirability of doing so is evident.

One of the problems in formulating suitable water-based functional fluids has been the selection of thickening agents that provide the desired degree of thickening and at the same time are stable under high shear conditions. Various thickeners have been tried, but none have been found to be entirely acceptable. Among the thickeners that have been tried are the polysaccharides, cellulose ethers and esters, and various synthetic polymers. The polysaccharides include the natural gums such as gum agar, guar gum, gum Arabic, algin, the dextrans, xanthan gum and the like. The cellulose ethers and esters include hydroxy hydrocarbyl cellulose and hydrocarbyl hydroxy cellulose and their salts. Included in this group are hydroxyethyl cellulose and the sodium salt of carboxy methyl cellulose. The synthetic polymers include polyacrylates, polyacrylamides, hydrolyzed vinyl esters, water-soluble homo- and interpolymers of acrylamidoalkane sulfonates containing 50 mole percent at least of acryloamido alkane sulfonate and other comonomers such as acrylonitrile, styrene and the like. Others include poly-n-vinyl pyrrolidones, homo- and copolymers as well as water-soluble salts of styrene, maleic anhydride and isobutylene maleic anhydride, copolymers.

It has been suggested to use certain water-soluble hydroxy terminated polyoxyalkylenes as thickening agents. See, for example, U.S. Pat. Nos. 3,005,776; 3,346,501; 4,138,346; and 4,151,099. The degree of thickening provided by these polyoxyalkylenes has not, however, been found to be entirely acceptable.

U.S. Pat. No. 4,288,639 discloses the use of certain alpha-olefin oxide-modified polyoxyalkylenes as thickeners for aqueous liquids. This patent indicates that these thickeners are obtained by capping a liquid straight-chain polyoxyalkylene heteric or block copolymer intermediate with an alpha-olefin oxide.

There remains a need for water-dispersible thickening agents that can provide water-based functional fluids with desired levels of thickening and are sufficiently stable for high shear applications.

SUMMARY OF THE INVENTION

Water-dispersible alkenyl-substituted carboxylic agent/hydroxy terminated polyoxyalkylene reaction products are provided in accordance with the present invention. These reaction products are useful as thickeners for water-based functional fluids, and are relatively stable for high shear applications.

Broadly stated, the present invention contemplates the provision of a composition comprising the water-dispersible reaction product of (A) at least one compound represented by the formula

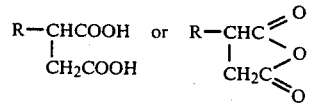

wherein R is an alkenyl group represented by the formula

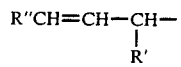

and R' and R" are independently hydrogen or straight chain or substantially straight chain hydrocarbyl groups of at least one carbon atom, with the proviso that R has from about 8 to about 30 carbon atoms, with (B) at least one water-soluble hydroxy terminated polyoxyalkylene. Aqueous concentrates and water-based functional fluids comprising these reaction products are also disclosed.

DESCRIPTION OF THE PREFERRED EMBODIMENT.

The terms "dispersed" and "dissolved" (and cognate terms such as "dispersion", "dispersible", "solution", "soluble", etc.) are used throughout this specification and in the appended claims to refer to the distribution of the compositions of the invention in the aqueous systems to which they are added. While the practice of the present invention is not dependent on any particular theory or hypothesis to explain the invention, it should be understood that in some instances, the compositions of the invention may dissolve in the aqueous phase to form true solutions while in other instances, micelle dispersions or micro-emulsions may be formed which visibly appear to be true solutions. Whether a solution, micelle dispersion, or micro-emulsion is formed, is dependent on the particular composition employed and the particular system to which it is added. In any event, the terms "dispersed" and "dissolved" are used interchangeably throughout this specification and in the appended claims to refer to solutions, micelle dispersions, micro-emulsions and the like.

COMPONENT (A)

The hydrocarbyl-substituted carboxylic acylating agents (A) used in making reaction products of the present invention are represented by the formula

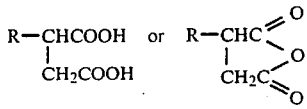

wherein R is an alkenyl group having from about 8 to about 30 carbon atoms, preferably from about 14 to about 24 carbon atoms, and more preferably from about 16 to about 18 carbon atoms and is represented by the formula

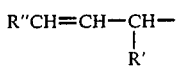

R' and R" are independently hydrogen or straight chain or substantially straight chain hydrocarbyl groups of at least 1 carbon atom, preferably from 1 to about 27 carbon atoms, more preferably from 1 to about 21 carbon atoms, more preferably from 1 to about 15 carbon atoms, and advantageously from 1 to about 13 carbon atoms, or mixtures of such groups; with the proviso that the total number of carbon atoms in R is within the above indicated ranges. Preferably R' and R" are alkyl or alkenyl groups. In a particularly advantageous embodiment, R has from about 16 to about 18 carbon atoms. R' is hydrogen or an alkyl or alkenyl group of from 1 to about 7 carbon atoms or a mixture thereof, and R" is an alkyl or alkenyl group of from about 5 to about 15 carbon atoms or a mixture thereof.

The term "hydrocarbyl" (and cognate terms such as hydrocarbyloxy, hydrocarbylmercapto, etc.) is used herein to include substantially hydrocarbyl groups (for example, substantially hydrocarbyloxy, substantially hydrocarbylmercapto, etc.), as well as purely hydrocarbyl groups. The description of these groups as being substantially hydrocarbyl means that they contain no non-hydrocarbyl substituents or non-carbon atoms which significantly affect the hydrocarbyl characteristics or properties of such groups relevant to their uses as described herein.

Examples of substituents which usually do not significantly alter the hydrocarbyl characteristics or properties of the general nature of the hydrocarbyl groups of this invention are the following:

Ether groups (especially hydrocarbyloxy such as methoxy, n-butoxy, etc.)

Oxo groups (e.g., —O— linkages in the main carbon chain)

Nitro groups

Thioether groups

Thia groups (e.g., —S— linkages in the main carbon chain)

Carbohydrocarbyloxy groups (e.g.,

hydrocarbyl)

Sulfonyl groups (e.g.,

hydrocarbyl)

Sulfinyl groups (e.g.,

hydrocarbyl)

This list is intended to be merely illustrative and not exhaustive, and the omission of a certain class of substituent is not meant to require its exclusion. In general, if such substituents are present, there will not be more than two for each ten carbon atoms in the substantially hydrocarbyl group and preferably not more than one for each ten carbon atoms. Nevertheless, the hydrocarbyl groups are preferably free from non-hydrocarbon groups; that is, they are preferably purely hydrocarbyl groups consisting of only carbon and hydrogen atoms.

The term "substantially straight chain" is used herein to refer to hydrocarbyl groups that have straight chains and contain no branching that adversely affects the thickening characteristics of the reaction products of components (A) and (B). For example, in the context of this invention, a straight chain $C_{16}$ alkyl group with a methyl group attached as a side or branch chain, and a straight chain $C_{16}$ alkyl group are substantially similar in their properties with regard to their use in this invention.

The alkenyl group can be derived from one or more olefins of from about 8 to about 30 carbon atoms. These olefins are preferably alpha-olefins (sometimes referred to as mono-1-olefins) or isomerized alphaolefins. Examples of the alpha olefins include 1-octene, 1-nonene, 1-decene, 1-dodecene, 1-tridecene, 1-tetradecene, 1-pentadecene, 1-hexadecene, 1-heptadecene, 1-octadecene, 1-nonadecene, 1-eicosene, 1-henicosene, 1-docosene, 1-tetracosene, 1-pentacosene, 1-hexacosene, 1-octasosense, 1-nonacosene, etc. Commercially available alpha olefin fractions that can be used include the $C_{15-18}$ alpha-olefins, $C_{12-16}$ alpha-olefins, $C_{14-16}$ alpha-olefins, $C_{14-18}$ alpha-olefins, $C_{16-18}$ alpha-olefins, $C_{16-20}$ alpha-olefins, $C_{22-28}$ alpha-olefins, etc. The $C_{16}$ and $C_{16-18}$ alpha-olefins are particularly preferred. Procedures for the preparation of these alpha-olefins are well known to those skilled in the art and are described, for example, under the heading "Olefins" in the *Encyclopedia of Chemical Technology*, Second Edition, Kirk and Othmer, Supplement, pages 632–657, Interscience Publishers, Div. of John Wiley and Son, 1971, which is hereby incorporated by reference for its relevant disclosures pertaining to methods for preparing alpha-olefins.

Isomerized alpha-olefins are alpha-olefins that have been converted to internal olefins (i.e., olefins wherein the olefinic unsaturation is other than in the "-1-" or alpha position). The isomerized alpha-olefins suitable for use herein are usually in the form of mixtures of internal olefins with some alpha-olefins present. The procedures for isomerizing alpha-olefins are well known in the art. Briefly these procedures usually involve contacting an alpha-olefin with a cation exchange resin at a temperature in the range of, for example, about 80° C. to about 130° C. until the desired degree of isomerization is achieved. These procedures are described, for example, in U.S. Pat. No. 4,108,889 and European Patent Application No. 20,037, which are incorporated herein by reference.

Generally, the alkenyl-substituted carboxylic acylating agents (A) are prepared by reacting the above-described alpha-olefins or isomerized alpha-olefins with the desired unsaturated carboxylic acid such as fumaric acid or derivative thereof such as maleic anhydride at a temperature in the range of, for example, about 160° C. to about 240° C., preferably about 185° C. to about 210° C., and more preferably about 190° C. Generally these reactions are conducted at an atmospheric pressure although pressures of up to about 100 psi can be used, particularly when the olefin has a relatively low molecular (e.g., $C_8$ to $C_{12}$). Free radical inhibitors (e.g., t-butyl catachol) can be used to reduce or prevent the formation of polymeric by-products. The procedures for preparing these hydrocarbylsubstituted carboxylic acylating agents are well known to those skilled in the art and have been described, for example, in U.S. Pat. No. 3,412,111; Japanese Kokai Tokkyo Koho 81 12,382 and 82 35,580; Benn et al, "The Ene Reaction of Maleic Anhydride With Alkenes", J. C. S. Perkin II, (1977), pp. 535-7; Remond, "Preparation-Properties et. Emplois de L'Anhydride Dodecenylsuccinique", *Revue Des Products Cliniques,* (Feb. 28, 1962) pp. 57-64, which are incorporated herein by reference.

COMPONENT B

The water-soluble hydroxy terminated polyoxyalkylenes (B) of the present invention are constituted of block polymers of propylene oxide and ethylene oxide, and a nucleus which is derived from organic compounds containing a plurality of reactive hydrogen atoms (these organic compounds hereinafter being referred to as "reactive hydrogen compounds"). The block polymers are attached to the nucleus at the sites of the reactive hydrogen atoms.

In a preferred embodiment, the reactive hydrogen compounds contain at least one nitrogen atom and from about two to about six reactive hydrogen atoms. At least one of the reactive hydrogen atoms is preferably attached to a nitrogen atom. An exception is in the case where the reactive hydrogen compound is derived from a reactive hydrogen compound in which one or more reactive hydrogen atoms were attached to a nitrogen atom. Triisopropanolamine, derived from ammonia and propylene oxide, is an example of the latter. The expression "reactive hydrogen atom" is used in this specification and the appended claims to mean a compound which contains a hydrogen atom which is sufficiently able to open the epoxide ring of 1,2-propylene oxide and will react with methyl magnesium iodide to liberate methane in the classical Zerewitinoff reaction (see Niederl and Niederl, Micromethods of Quantitative Organic Anaylsis, page 263, John Wiley & Sons, New York City, 1946).

Generally, the nitrogen-containing reactive hydrogen compounds have up to about six carbon atoms. Examples include ammonia, primary amines, alkylene polyamines, alkanolamines and heterocyclic nitrogen compounds. Thus, primary amines having not over six carbon atoms such as methylamine, ethylamine, propylamine, butylamine, amylamine, hexylamine and aniline are satisfactory. Alkylene polyamines, especially aliphatic primary diamines, having not over six carbon atoms can be used. These include ethylenediamine, diethylenetriamine, triethylenetetramine, tetraethylenepentamine, hexamethylenediamine, phenylenediamine and the like. Alkanolamines having not over six carbon atoms can be used such as monoethanolamine, diethanolamine, triethanolamine, isopropanolamine, tri(2-propanol)amine, 2-amino-1-butanol, N-butyl-di(2-propanol)amine and the like. Furthermore, heterocyclic nitrogen compounds containing a hetero N atom can be employed, such as piperazine, 2-methylpiperazine, 2,5-dimethylpiperazine, imidazimidazole, pyrazolidine, pyrazolidone, hydantoin, dimethylhydantoin and the like. Hydroxyl amine and the hydroxylamine derivatives and aminophenol and aminophenol derivatives can also be used.

The reactive hydrogen compounds also include the polyhydric alcohols having from about two to about ten carbon atoms and from about two to about six hydroyl groups. These include, for example, alkane alcohols, such as, ethylene glycol, propylene glycol, 1,4-butane diol, 1,2-butane diol, trimethylol-propane, glycerol, 2,3,5,6-hexane tetrol, glucose, sorbitol, pentaerythritol, and the like; alkene alcohols, such as, 2-butene-1,4-diol, 1,5-hexadiene-3,4-diol, 2-hexene-1,4,6-triol, 3-heptene-1,2,6,7-tetrol, and the likes; alkyne alcohols, such as 2-butyne-1,4-diol, 2-hexyne-1,4,6-triol, 4-octyne-1,2,7,8-tetrol, and the like; and oxyalkylene alcohols, such as diethylene glycol, triethylene glycol, tetraethylene glycol, dipropylene glycol, tripropylene glycol, and the like.

In a preferred embodiment, chains of oxypropylene groups are attached to the reactive hydrogen compound at the sites of the reactive hydrogen atoms or hydroxyl groups. Chains of oxyethylene groups are then attached to the ends of the oxypropylene chains. These polyoxyalkylenes are prepared by reacting propylene oxide with the reactive hydrogen compound and subsequently reacting ethylene oxide with the propylene oxide-reactive hydrogen compound reaction product.

Alternatively, chains of oxyethylene groups are attached to the reactive hydrogen compound at the sites of the reactive hydrogen atoms or hydroxyl groups. Chains of oxypropylene groups are then attached to the ends of the oxyethylene chains. These polyoxyalkylenes are prepared by reacting ethylene oxide with the reactive hydrogen compound and subsequently reacting propylene oxide with the ethylene oxide-reactive hydrogen compound reaction product.

It is not necessary to use pure propylene oxide in producing the oxypropylene chains, although this is preferred. Small amounts, for example up to about 5 weight percent, of ethylene oxide can be included in the propylene oxide employed to prepare such chains. In this connection, the ethylene oxide used to prepare the oxyethylene chains can also contain small amounts, such as up to about 5 weight percent, of propylene oxide.

It is well recognized in the field of alkylene oxide chemistry that the polyoxyalkylene compositions one obtains by reacting an alkylene oxide with a reactive hydrogen compounds are actually mixtures of compounds rather than a single molecular compound. The mixture contains closely related homologs wherein the statistical average number of oxyalkylene groups equals the number of mols of the alkylene oxide employed and the individual members in the mixture contain varying numbers of oxyalkylene groups.

The reaction of propylene oxide (or ethylene oxide) with the reactive hydrogen compound and the subsequent reaction of ethylene oxide (or propylene oxide) therewith are carried out in the known manner for condensing alkylene oxides with reactive hydrogen compounds. The process is normally carried out at elevated temperatures and pressures in the presence of alkaline catalysts, such as sodium hydroxide, potassium hydroxide, sodium alkoxide, quaternary ammonium bases, and the like. The reactions can also be carried out in the presence of acid catalysts. The manipulative steps will vary to some extent depending upon the normal physical state of the reactive hydrogen compound. Certain of these compounds are normally gases, e.g., ammonia and methylamine, and propylene oxide can be condensed with these compounds by carrying out the reaction under sufficient pressure to liquefy the reactive hydrogen compound, or the normally gaseous reactive hydrogen compound can be dissolved in an inert solvent. Similarly, if the reactive hydrogen compound is a solid at reaction temperatures, it is normally dissolved in an inert solvent. After a few mols of propylene oxide (or ethylene oxide) have been condensed with the reactive hydrogen compound, the adduct becomes a liquid and the inert solvent can be removed by distillation. Thereafter, it is preferred to simply add the propylene oxide (or ethylene oxide) to the liquid reaction mixture without the use of a solvent.

In a particularly advantageous embodiment of the invention the hydroxy-terminated polyoxyalkylenes (B) are represented by the formula

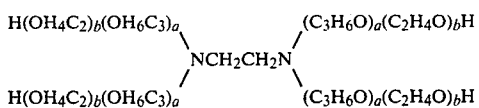

wherein a and b are integers such that the collective molecular weight of the oxypropylene chains range from about 900 to about 25,000, and the collective weight of the oxyethylene chains constitute from about 20% to about 90%, preferably about 25% to about 55% by weight of the compound. These compounds are commercially available from BASF Wyandotte Corporation under the tradename "Tetronic".

In another particularly advantageous embodiment, the hydroxy-terminated polyoxyalkylenes (B) are represented by the formula

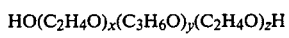

wherein y is an integer such that the molecular weight of the oxypropylene chain is at least about 900, and x and z are integers such that the collective weight of the oxyethylene chains constitute from about 20% to about 90% by weight of the compound. These compounds preferably have a molecular weight in the range of about 1100 to about 14,000. These compounds are commercially available from BASF Wyandotte Corporation under the tradename "Pluronic".

Preparations of hydroxy-terminated polyoxyalkylenes that are useful in accordance with the present invention are disclosed in U.S. Pat. Nos. 2,674,619 and 2,979,528, which are incorporated herein by reference.

REACTION OF COMPONENTS (A) AND (B)

The reaction of the carboxylic agent (A) with the hydroxy-terminated polyoxyalkylene (B) can be carried out at temperatures ranging from the highest of the melt temperatures of the reaction components up to the lowest of the decomposition temperatures of the reaction components or products. Generally, it is carried out at a temperature in the range of about 60° C. to about 160° C., preferably about 120° C. to about 160° C. Usually the reaction is carried out under ester-forming conditions and the product thus formed is, for example, a half-ester, i.e., an ester/acid.

Generally the ratio of equivalents of component (A) to component (B) ranges from about 0.5:1 to about 8:1, preferably about 2:1 to about 5:1, and advantageously about 4:1. The weight of an equivalent of component (A) can be determined by dividing its molecular weight by the number of carboxylic functions present. With component (A), the weight of an equivalent is equal to one-half of its molecular weight. The weight of an equivalent of the hydroxy-terminated polyoxyalkylene (B) can be determined by dividing its molecular weight by the number of hydroxyl groups present. These can usually be determined from the structural formula of the hydroxyterminated polyoxyalkylene or empirically through well known procedures.

The ester/acids formed by the reaction of components (A) and (B) can be neutralized with, for example, one or more alkali metals, one or more amines, or a mixture thereof, and thus converted to ester/salts. Additionally, if these ester/acids are added to concentrates or functional fluids containing alkali metals or amines, ester/salts usually form, in situ.

Among the alkali metals that can be used to neutralize these ester/acids and thus form such ester/salts are sodium, potassium and lithium. Suitable metal bases include the free metals and their oxides, hydroxides, alkoxides and basic salts. Examples are sodium hydroxide, sodium methoxide, sodium carbonate, potassium hydroxide, potassium carbonate, and the like. Generally the ratio of moles of alkali metal to equivalents of acid in the ester/acid is in the range of about 1:10 to about 2:1, preferably about 1:1. The weight of an equivalent of acid in these ester/acids can be determined by dividing the molecular weight of the ester/acid by the number of —COOH groups present. These can usually be determined from the structural formula of the ester/acid or empirically through well known titration procedures.

Among the amines that can be used to neutralize these ester/acids are the N-(hydroxyl-substituted hydrocarbyl)amines. These amines generally have one to about four, typically one to about two hydroxyl groups per molecule. These hydroxyl groups are each bonded to a hydrocarbyl group to form a hydroxyl-substituted hydrocarbyl group which, in turn, is bonded to the amine portion of the molecule. These N-(hydroxyl-substituted hydrocarbyl)amines can be monoamines or polyamines and they can have a total of up to about 40 carbon atoms; generally they have a total of about 20 carbon atoms. They can be monoamines containing but a single hydroxyl group. These amines can be primary, secondary or tertiary amines while the N-(hydroxyl-substituted hydrocarbyl)polyamines can have one or more of any of these types of amino groups. Mixtures of two or more of any of the afore-described amines can also be used.

Generally the ratio of moles of amine to equivalents of ester/acid is in the range of about 1:10 to about 10:1, preferably about 1:1.

The alkali metal or amine is preferably added after the reaction between components (A) and (B) is completed, i.e., to the resulting ester/acid. Generally, the addition of alkali metal or ester salt is made at a temperature in the range of the highest of the melt temperatures of the ester/acid, or amine or metal base for the alkali metal up to the lowest of the decomposition temperatures of such materials. The temperature is preferably in the range of about 60° C. to about 160° C., more preferably about 120° C. to about 160° C.

The following examples describe exemplary preparations of water-dispersible alkenyl-substituted carboxylic acylating agent/hydroxy terminated polyoxyalkylene reaction products of the present invention. Unless otherwise indicated, all parts and percentages are by weight.

EXAMPLE 1

1700 parts of Tetronic 908 (a product of BASF Wyandotte Corporation identified as a hydroxy-terminated polyoxyalkylene constituted of block polymers of propylene oxide and ethylene oxide and a nucleus derived from ethylene diamine and having a molecular weight of 27,000) and 136 parts of Hysize B (a product of Humphrey Chemical Company identified as a $C_{16}$ isomerized alpha-olefin substituted succinic anhydride) are are added to a 5-liter flash and heated to 160°–170° C. for 3 hours to provide the desired product.

EXAMPLE 2

272 parts of Hysize B and 3400 parts of Tetronic 908 are added to a 5-liter flask and heated to 160°–170° C. for three hours. The resulting product is cooled to 140° C. and 220 parts of Ethomeen T-15 (a product of Armak Company identified as a mixture of ethoxylated fatty amines) are added. The mixture is cooled with stirring to 125° C., then cooled to room temperature to provide the desired product.

EXAMPLE 3

Part A 2960 parts of $C_{16}$ alpha-olefin and 100 parts of Amberlyst 15 (a product of Rohm & Haas Company identified as a cation exchange resin) are added to a five-liter flask equipped with a nitrogen sparge (2.0 standard cubic feet per hour), stirrer, thermowell and water trap positioned below a condenser. The mixture is heated to 120° C. with the stirrer operating at 350 rpm. After 1.5 hours, 870 parts of the desired product are withdrawn.

Part B 367.5 parts of maleic anhydride are added to a two-liter flask equipped with stirrer, thermowell, reflux condenser and gas inlet tube. The maleic anhydride is melted and 765 parts of the product from Part A are added. The mixture is heated to 180°–200° C. for 9.75 hours. The mixture is stripped under a vacuum of 30 mm. Hg. at 182° C., then cooled to 115° C. The mixture is then stripped under a vacuum of 0.7 mm. Hg. at 145° C., then cooled to 50° C. The mixture is filtered with diatomaceous earth. The filtrate is the desired product.

Part C 160 parts of the product from Part B and 6250 parts of Tetronic 908 are added to a 12-liter flask and heated to 155°–162° C. for four hours, then cooled to room temperature to provide the desired product.

EXAMPLE 4

Part A 1100 parts of a $C_{16-18}$ alpha-olefin fraction and 14 parts of Amberlyst 15 are added to a two-liter flask equipped with stirrer, thermowell, reflux condenser and stopper. The mixture is heated to 150°–155° C. for 3.25 hours, then filtered. The filtrate is the desired product.

Part B 412 parts of maleic anhydride and 920 parts of the product of Part A are added to a two-liter flask equipped with stirrer, thermowell, reflux condenser and stopper. The mixture is heated to 90° C. Stirring is commenced. The mixture is heated to 190°–195° C. with stirring and maintained at that temperature for 11.5 hours, then cooled to 80° C. The mixture is stripped under a vacuum of 38 mm. Hg. at a temperature of 120° C. The mixture is then stripped under a vacuum of 0.45 mm. Hg. at 180° C. The mixture is filtered with diatomaceous earth. The filtrate is the desired product.

Part C 166 parts of the product from Part B and 6250 parts of Tetronic 908 are added to a 12-liter flask and heated to 155°–158° C. The temperature is maintained in that range for four hours. The mixture is then cooled to room temperature to provide the desired product.

EXAMPLE 5

Part A 5775 parts of a $C_{15-18}$ alpha-olefin fraction (having a carbon number distribution of 1% $C_{14}$, 29% $C_{15}$, 28% $C_{16}$, 27% $C_{17}$, 14% $C_{18}$, and 1% $C_{19}$) are passed through a 12-inch column packed with activated alumina into a 12-liter flask containing maleic anhydride. The mixture is heated to 214° C. and maintained at that temperature for 7 hours with a nitrogen sparge (0.2 standard cubic feet per hour) and then cooled to room temperature. The mixture is then heated to 209°–212° C. and maintained at that temperature for 7 hours, then cooled to room temperature. 1500 parts of textile spirits are added and the mixture is stirred for one hour. The mixture is filtered with diatomaceous earth. The mixture is stripped under a vacuum of 30 mm. Hg. at 121° C., then cooled to room temperature. The mixture is then stripped under a vacuum of 0.7 mm. Hg at 168° C. then cooled to room temperature. The mixture is filtered with diatomaceous earth at room temperature. The filtrate is the desired product.

Part B 160 parts of the product from Part A and 6250 parts of Tetronic 908 are added to a 12-liter flask and heated to 158°–165° C. for 4 hours, then cooled to room temperature to provide the desired product.

EXAMPLE 6

Part A

A 20-liter kettle is purged with nitrogen. 475 parts of a $C_{18-24}$ alpha-olefin fraction are charged to the kettle. The kettle contents are heated to 71° C. and mixed. 189 parts maleic anhydride are added. The mixture is heated to 200° C. over a 6-hour period; the temperature in- Specific examples of the N-(hydroxyl-substituted hydrocarbyl)amines suitable for use in this invention are the N-(hydroxy-lower alkyl)amines and polyamines such as 2-hydroxyethylamine, 3-hydroxybutylamine, di-(2-hydroxyethyl)amine, tri-(2-hydroxyethyl)amine, di-(2-hydroxypropyl)amine, N,N,N'-tri-(2-hydroxyethyl)ethylenediamine, N,N,N',N'-tetra(2-hydroxyethyl)ethylenediamine, N-(2-hydroxyethyl)piperazine, N,N'-di-(3-hydroxypropyl)piperazine, N-(2-hydroxyethyl)-morpholine, N-(2-hydroxyethyl)-2-morpholinone, N-(2-hydroxyethyl)-3-methyl-2-morpholinone, N-(2-hydroxypropyl)-6-methyl-2-morpholinone, N-(2-hydroxypropyl)-5-carbethoxy-2-piperidone, N-(2-hydroxypropyl)-5-carbethoxy-2-piperidone, N-(2-hydroxyethyl)-5-(N-butylcarbamyl)-2-piperidone, N-(2-hydroxyethyl)piperidine, N-(4-hydroxybutyl)piperidine, N,N-di-(2-hydroxyethyl)glycine, and ethers thereof with aliphatic alcohols, especially lower alkanols, N,N-di(3-hydroxypropyl)glycine, and the like.

Further amino alcohols are the hydroxy-substituted primary amines described in U.S. Pat. No. 3,576,743 by the general formula $$R_a\text{—}NH_2$$

wherein $R_a$ is a monovalent organic radical containing at least one alcoholic hydroxy group. According to this patent, the total number of carbon atoms in $R_a$ will not exceed about 20. Hydroxy-substituted aliphatic primary amines containing a total of up to about 10 carbon atoms are useful. Generally useful are the polyhydroxy-substituted alkanol primary amines wherein there is only one amino group present (i.e., a primary amino group) having one alkyl substituent containing up to 10 carbon atoms and up to 4 hydroxyl groups. These alkanol primary amines correspond to $R_aNH_2$ wherein $R_a$ is a mono- or polyhydroxy-substituted alkyl group. It is typical that at least one of the hydroxyl groups be a primary alcoholic hydroxyl group. Trismethylolaminomethane is a typical hydroxy-substituted primary amine. Specific examples of the hydroxy-substituted primary amines include 2-amino-1-butanol, 2-amino-2-methyl-1-propanol, p-(betahydroxyethyl)analine, 2-amino-1-propanol, 3-amino-1-propanol, 2-amino-2-methyl-1,3-propanediol, 2-amino-2-ethyl-1,3-propanediol, N-(betahydroxypropyl)-N'-beta-aminoethyl)piperazine, 2-amino-1-butanol, ethanolamine, beta-(betahydroxy ethoxy)-ethyl amine, glucamine, glusoamine, 4-amino-3-hydroxy-3-methyl-1-butene (which can be prepared according to procedures known in the art by reacting isopreneoxide with ammonia), N-3-(aminopropyl)-4(2-hydroxyethyl)-piperadine, 2-amino-6-methyl-6-heptanol, 5-amino-1-pentanol, N-(betahydroxyethyl)-1,3-diamino propane, 1,3-diamino-2-hydroxy-propane, N-(beta-hydroxy ethoxyethyl)-ethylenediamine, and the like. For further description of the hydroxy-substituted primary amines useful as the N-(hydroxyl-substituted hydrocarbyl)amines in this invention see U.S. Pat. No. 3,576,743 which is incorporated herein by reference.

Typically, the amine is a primary, secondary or tertiary alkanol amine or mixture thereof. Such amines can be represented, respectively, by the formulae:

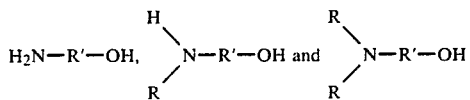

wherein each R is independently a hydrocarbyl group of 1 to about 8 carbon atoms or hydroxyl-substituted hydrocarbyl group of 2 to about 8 carbon atoms and R' is a divalent hydrocarbyl group of about 2 to about 18 carbon atoms. The group —R'—OH in such formulae represents the hydroxyl-substituted hydrocarbyl group. R' can be an acyclic, alicyclic or aromatic group. Typically, it is an acyclic straight or branched alkylene group such as an ethylene, 1,2-propylene, 1,2-butylene, 1,2-octadecylene, etc. group. Where two R groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each R is a lower alkyl group of up to 7 carbon atoms.

The amine can also be an ether N-(hydroxyl-substituted hydrocarbyl)amine. Such amines can be conveniently prepared by reaction of epoxides with aforedescribed amines and can be represented by the formulae:

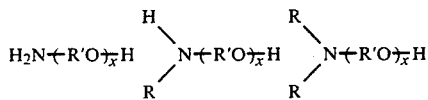

wherein x is a number from 2 to about 15 and R and R' are as described above.

Polyamine analogs of these alkanol amines, particularly alkoxylated alkylene polyamines (e.g., N,N-(diethanol)ethylene diamine) can also be used. Such polyamines can be made by reacting alkylene amines (e.g., ethylene diamine) with one or more alkylene oxides (e.g., ethylene oxide, octadecene oxide) of two 2 to about 20 carbons. Similar alkylene oxide-alkanol amine reaction products can also be used such as the products made by reacting the afore-described primary, secondary or tertiary alkanol amines with ethylene, propylene or higher epoxides in a 1:1 or 1:2 molar ratio. Reactant ratios and temperatures for carrying out such reactions are known to those skilled in the art.

Specific examples of alkoxylated alkylene polyamines include N-(2-hydroxyethyl)ethylene diamine, N,N-bis(2-hydroxyethyl)-ethylene diamine, 1-(2-hydroxyethyl)piperazine, mono(hydroxypropyl)-substituted diethylene triamine, di(hydroxypropyl)-substituted tetraethylene pentamine, N-(3-hydroxybutyl)-tetramethylene diamine, etc. Higher homologs obtained by condensation of the above-illustrated hydroxy alkylene polyamines through amino radicals or through hydroxy radicals are likewise useful. Condensation through amino radicals results in a higher amine accompanied by removal of ammonia while condensation through the hydroxy radicals results in products containing ether linkages accompanied by removal of water. Mixtures of two or more of any of the afore-described mono- or polyamines are also useful.

creasing at a rate of 22° C. per hour. The mixture is then heated to 220° C. over a 4-hour period; the temperature increasing at a rate of 5° C. per hour. The temperature is maintained at 220° C. for 10 hours. The mixture is blown with nitrogen until the level of unreacted maleic anhydride is about 0.05% and then cooled to room temperature to provide the desired product.

Part B 206 parts of the product of Part A and 6250 parts of Tetronic 908 are added to a 12-liter flask and heated to 160°–170° C. and maintained at that temperature for 4 hours to provide the desired product.

Concentrates and Water-Based Functional Fluids

The invention includes aqueous systems or compositions characterized by an aqueous phase with the reaction product of components (A) and (B) dispersed in said aqueous phase. Preferably, this aqueous phase is a continuous aqueous phase. These aqueous systems usually contain at least about 70% by weight water. Such aqueous systems encompass both concentrates containing about 70% to about 90%, preferably about 75% to about 85% water; and water-based functional fluids containing a major amount of water and a minor thickening amount of the reaction product of components (A) and (B), preferably from about 1.5% to about 10%, more preferably about 3% to about 6% by weight of said reaction product. The concentrates generally contain less than about 50%, preferably less than about 25%, more preferably less than about 15%, and still more preferably less than about 6% hydrocarbyl oil. The water-based functional fluids contain less than about 15%, preferably less than about 5%, and more preferably less than about 2% hydrocarbyl oil. These concentrates and water-based functional fluids can optionally include other conventional additives commonly employed in water-based functional fluids. These other additives include dispersant/solubilizers, surfactants, functional additives, corrosion-inhibitors, shear stabilizing agents, bactericides, dyes, water-softeners, odor masking agents, anti-foam agents, and the like.

The concentrates are analogous to the water-based functional fluids except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily by ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbyl oil.

Also included within the invention are methods for preparing aqueous systems, including both concentrates and water-based functional fluids, containing other conventional additives commonly employed in water-based functional fluids. These methods comprise the steps of:

(1) mixing the composition of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the composition of the invention and other functional additives in said concentrates or said water-based functional fluids.

These mixing steps are carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances the finished water-based functional fluid can be formed directly in the same equipment used to form the concentrate or the dispersion or solution.

The dispersant/solubilizers that are useful in accordance with the present invention include the nitrogen-containing, phosphorus-free carboxylic solubilizers disclosed in U.S. Pat. Nos. 4,329,249; 4,368,133; 4,435,297; 4,447,348; and 4,448,703. These patents are incorporated herein by reference. Briefly, these dispersant/solubilizers are made by reacting (I) at least one carboxylic acid acylating agent having at least one hydrocarbyl-based substituent of at least about 12 to about 500 carbon atoms with (II) at least one (a) N-(hydroxyl-substituted hydrocarbyl)amine, (b) hydroxyl-substituted poly(hydrocarbyloxy) analog of said amine (a), or (c) mixtures of (a) and (b). Preferred acylating agents include the substituted succinic acids or anhydrides. Preferred amines include the primary, secondary and tertiary alkanol amines or mixtures thereof. These dispersant/solubilizers are preferably used at effective levels to disperse or dissolve the various additives, particularly the functional additives discussed below, in the concentrates and/or water-based functional fluids of the present invention. In a particularly preferred embodiment of the present invention, the dispersant/solubilizer is the reaction product of a polyisobutenyl-substituted succinic anhydride with diethylethanolamine or a mixture of diethylethanolamine and ethanolamine.

The surfactants that are useful can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9–10 ethylene oxide units per molecule, has an HLB value of about 13.5 and a molecular weight of about 628. Many other suitable nonionic surfactants are known; see, for example, the aforementioned McCutcheon's as well as the treatise "Non-ionic Surfactants" edited by Martin J. Schick, M. Dekker Co., New York, 1967, which is hereby incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the well-known quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

These surfactants, when used, are generally employed in effective amounts to aid in the dispersal of the various additives, particularly the functional additives discussed below, in such systems.

The functional additives that can be used are typically oil-soluble, water-insoluble additives which function in conventional oil-based systems as E.P. agents, anti-wear agents, load-carrying agents, friction modifiers, lubricity agents, etc. They can also function as anti-slip agents, film formers and friction modifiers. As is well known, such additives can function in two or more of the above-mentioned ways; for example, E.P. agents often function as load-carrying agents.

The term "oil-soluble, water-insoluble functional additive" refers to a functional additive which is not soluble in water above a level of about 1 gram per 100 milliliters of water at 25°, but is soluble in mineral oil to the extent of at least one gram per liter at 25°.

These funtional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369–392, and West German Published Patent Application No. 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acid and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Mainly such functional additives are known to the art. For example, descriptions of additives useful in conventional oil-based systems and in the aqueous systems of this invention are found in "Advances in Petroleum Chemistry and Refining," Volume 8, Edited by John J. McKetta, Interscience Publishers, New York, 1963, pages 31–38 inclusive; Kirk-Othmer "Encyclopedia of Chemical Technology," Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the systems of this invention.

In certain of the typical aqueous systems of the invention, the functional additive is a sulfur or chloro-sulfur E.P. agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of phosphorodithioic acid, such as zinc dicyclohexyl phosphorodithioate, and the zinc salts of a phosphorodithioic acid.

The functional additive can also be a film former such as a synthetic or natural latex or emulsion thereof in water. Such latexes include natural rubber latexes and polystyrene butadienes synthetic latex.

The functional additive can also be an antichatter or anti-squawk agent. Examples of the former are the amide metal dithiophosphate combinations such as disclosed in West German Pat. No. 1,109,302; amine salt-azomethene combinations such as disclosed in British Patent Specification No. 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous systems of this invention include the following commercially available products.

TABLE I

| Functional Additive Tradename | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |
| Emcol TS 230 | Acid phosphate ester | Witco[3] |

[1]The Lubrizol Corporation, Wickliffe, Ohio, U.S.A.
[2]R. T. Vanderbilt Company, Inc., New York, N.Y., U.S.A.

Mixtures of two or more of any of the aforedescribed functional additives can also be used.

Typically, a functionally effective amount of the functional additive is present in the aqueous systems of this invention. For example, if the functional additive is intended to serve primarily as a load-carrying agent, it is present in a load-carrying amount.

The aqueous systems of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596–605. This disclosure relative to inhibitors are hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tertiarybutyl benzoic acid), neutralized naphthenic acids and neutralized hydrocarbyl sulfonates. Mixed salt esters of alkylated succinimides are also useful. Particularly useful amines include the alkanol amines such as ethanol amine, diethanol amine, triethanol amine and the corresponding propanol amines. Mixtures of two or more of any of the afore-described corrosion inhibitors can also be used. The corrosion inhibitor is usually present in concentrations in which they are effective in inhibiting corrosion of metals with which the aqueous composition comes in contact.

Certain of the aqueous systems of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and worktool, the polyol of inverse solubility "plates out" on the surface of the workpiece, thus improving its lubricity characteristics.

The aqueous systems of the present invention can also include at least one bacteriocide. Such bacteriocides are well known to those of skill in the art and specific examples can be found in the aforementioned McCutcheon publication "Functional Materials" under the heading "Antimicrobials" on pages 9–20 thereof. This disclosure is hereby incorporated by reference as it relates to suitable bacteriocides for use in the aqueous compositions or systems of this invention. Generally, these bacteriocides are water-soluble, at least to the extent to allow them to function as bacteriocides.

The aqueous systems of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous systems of this invention may also include an anti-freeze additive where it is desired to use the composition at a low temperature. Materials such as ethylene glycol and analogous polyoxyalkylene polyols can be used as anti-freeze agents. Clearly, the amount used will depend on the degree of antifreeze protection desired and will be known to those of ordinary skill in the art.

It should also be noted that many of the ingredients described above for use in making the aqueous systems of this invention are industrial products which exhibit or confer more than one property on such aqueous systems. Thus, a single ingredient can provide several functions thereby eliminating or reducing the need for some other additional ingredient. Thus, for example, an E.P. agent such as tributyl tin oxide can also function as a bactericide.

Illustrative water-based functional fluids within the scope of this invention are disclosed in Table II. These functional fluids are prepared by mixing the ingredients at a temperature in the range of about 50° C. to about 70° C. using conventional mixing techniques. Preferably the thickeners of the invention (i.e., the Products of Examples 1–6) are added last. Each of the functional fluids identified below have application as hydraulic fluids. The numerical values indicated in Table II are in parts by weight.

TABLE II

| | A | B | C | D | E | F | G | H | I | J |
|---|---|---|---|---|---|---|---|---|---|---|
| Product of Example 1 | 6.00 | | | | | | | | | |
| Product of Example 2 | | 5.20 | | | | | | | | |
| Product of Example 3 | | | 3.50 | 5.00 | | | | | | |
| Product of Example 4 | | | | | 3.50 | 5.00 | | | | |
| Product of Example 5 | | | | | | | 3.50 | 5.00 | | |
| Product of Example 6 | | | | | | | | | 3.50 | 5.00 |
| Commercially available polyisobutenyl (950 mol. wt.) substituted succinic anhydride diethylethanolamine reaction product | 1.204 | 1.686 | 1.686 | 1.686 | 1.686 | 1.686 | 1.686 | 1.686 | 1.686 | 1.686 |
| Diethanolamine | 0.079 | 0.111 | 0.111 | 0.111 | 0.111 | 0.111 | 0.111 | 0.111 | 0.111 | 0.111 |
| Diethylethanolamine | 0.13 | 0.182 | 0.182 | 0.182 | 0.182 | 0.182 | 0.182 | 0.182 | 0.182 | 0.182 |
| Ethanolamine | 0.024 | 0.034 | 0.034 | 0.034 | 0.034 | 0.034 | 0.034 | 0.034 | 0.034 | 0.034 |
| Unitol DT-40, a product of Union Camp, identified as distilled tall oil | 0.245 | 0.343 | 0.343 | 0.343 | 0.343 | 0.343 | 0.343 | 0.343 | 0.343 | 0.343 |
| Diluent oil | 0.094 | 0.132 | 0.132 | 0.132 | 0.132 | 0.132 | 0.132 | 0.132 | 0.132 | 0.132 |
| Grotan, a commercial bactericide available from Lehn & Fink, Div. of Sterling Drug | 0.14 | 0.196 | 0.196 | 0.196 | 0.196 | 0.196 | 0.196 | 0.196 | 0.196 | 0.196 |
| Foamban MS-30, a commercial anti-foaming agent available from Ultra Adhesives, Inc. | 0.032 | 0.049 | 0.049 | 0.049 | 0.049 | 0.049 | 0.049 | 0.049 | 0.049 | 0.049 |
| Commercially available zinc salt of O,O—di (isooctyl) phosphorodithioic acid | 0.483 | 0.676 | 0.676 | 0.676 | 0.676 | 0.676 | 0.676 | 0.676 | 0.676 | 0.676 |
| Water | 91.57 | 91.40 | 93.46 | 91.96 | 93.46 | 91.96 | 93.46 | 91.96 | 93.46 | 91.96 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A composition comprising the water-dispersible ester/acid or ester/salt of (A) at least one compound represented by the formula

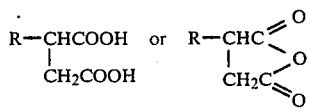

wherein R is an alkenyl group represented by the formula

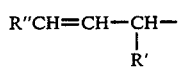

and R' and R" are independently hydrogen or straight chain or substantially straight chain hydrocarbyl groups of at least one carbon atom, with the proviso that R has from about 8 to about 30 carbon atoms, with (B) at least one water-soluble hydroxy terminated polyoxyalkylene, said polyoxyalkylene containing oxypropylene and oxyethylene chains and a nucleus derived from a reactive hydrogen compound based on a polyamine.

2. The composition of claim 1 wherein R has from about 12 to about 24 carbon atoms.

3. The composition of claim 1 wherein R has from about 16 to about 18 carbon atoms.

4. The composition of claim 1 wherein R is derived from an alpha-olefin or an isomerized alpha-olefin.

5. The composition of claim 1 wherein R is derived from a mixture of olefins.

6. The composition of claim 1 with said reactive hydrogen compound containing reactive hydrogen atoms and/or hydroxyl groups, said oxypropylene chains being attached to said reactive hydrogen compound at the sites of the reactive hydrogen atoms and/or hydroxyl groups, said oxyethylene chains being attached to the ends of said oxypropylene chains.

7. The composition of claim 1 with said reactive hydrogen compound containing reactive hydrogen atoms and/or hydroxyl groups, said oxyethylene chains being attached to said reactive hydrogen compound at the sites of the reactive hydrogen atoms and/or hydroxyl groups, said oxypropylene chains being attached to the ends of said oxyethylene chains.

8. The composition of claim 1 wherein said reactive hydrogen compound contains from about 2 to about 6 reactive hydrogen atoms and up to about 6 carbon atoms.

9. The composition of claim 1 wherein said reactive hydrogen compound contains from about 2 to about 6 hydroxyl groups and from about 2 to about 10 carbon atoms.

10. The composition of claim 1 wherein said reactive hydrogen compound is a primary alkyl amine, an alkylene polyamine, an alkanolamine, piperazine, a hydrocarbon-substituted alkylpiperazine, or an aminophenol.

11. The composition of claim 1 wherein said reactive hydrogen compound is ethylenediamine.

12. The composition of claim 1 wherein component (B) is a compound represented by the formula

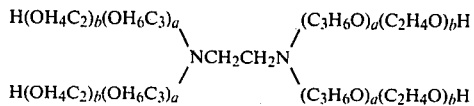

wherein a and b are integers such that the collective molecular weight of the oxypropylene chains is in the range of about 900 to about 25,000 and the collective molecular weight of the oxyethylene chains constitutes from about 20% to about 90% by weight of component (B).

13. The composition of claim 12 wherein component (B) has a molecular weight in the range of about 1650 to about 30,000.

14. The composition of claim 1 wherein the ratio of equivalents of component (A) to component (B) ranges from about 0.5:1 to about 8:1.

15. The composition of claim 1 wherein the ratio of equivalents of component (A) to component (B) ranges from about 2:1 to about 5:1.

16. The composition of claim 1 wherein the ratio of equivalents of component (A) to component (B) is about 4:1.

17. The composition of claim 1 wherein components (A) and (B) are reacted at a temperature ranging from the highest of the melt temperatures of components (A) and (B) up to the lowest of the decomposition temperatures of such components or said reaction product.

18. The composition of claim 1 wherein components (A) and (B) are reacted at a temperature in the range of about 60° C. to about 160° C.

19. A concentrate comprising water and from about 10% to about 30% by weight of the composition of any one of claims 1-18.

20. A water-based functional fluid comprising a major amount of water and a minor thickening amount of the composition of any one of claims 1-18.

* * * * *